(12) United States Patent
Mentzer et al.

(10) Patent No.: US 7,573,565 B1
(45) Date of Patent: Aug. 11, 2009

(54) METHODS AND SYSTEMS FOR DETERMINING THE DENSITY AND/OR TEMPERATURE OF FLUIDS

(75) Inventors: Mark A. Mentzer, Lititz, PA (US); Nicholas P. Petrillo, New Cumberland, PA (US); Wayne A. Webb, Lancaster, PA (US)

(73) Assignee: Strube, Inc., Marietta, PA (US)

( * ) Notice: Subject to any disclaimer, the term of this patent is extended or adjusted under 35 U.S.C. 154(b) by 201 days.

(21) Appl. No.: 11/649,109

(22) Filed: Jan. 3, 2007

Related U.S. Application Data

(60) Provisional application No. 60/782,002, filed on Mar. 14, 2006.

(51) Int. Cl.
*G01J 5/48* (2006.01)
(52) U.S. Cl. .......................... 356/44; 285/13; 374/130; 356/436
(58) Field of Classification Search ......... 356/432–440, 356/244, 246, 43, 44; 250/577, 574, 573, 250/901; 385/12, 13, 92; 374/130
See application file for complete search history.

(56) References Cited

U.S. PATENT DOCUMENTS

| 4,942,306 | A | * | 7/1990 | Colbourne | ................... 250/577 |
|---|---|---|---|---|---|
| 5,055,699 | A | * | 10/1991 | Konig et al. | ................. 250/577 |
| 5,115,811 | A | * | 5/1992 | Hartlaub et al. | ............. 600/342 |
| 5,646,354 | A | * | 7/1997 | Lovejoy | .................. 73/861.95 |
| 6,831,290 | B2 | | 12/2004 | Mentzer | |
| 6,888,636 | B2 | * | 5/2005 | Martino et al. | .............. 356/436 |
| 2003/0172752 | A1 | * | 9/2003 | Kluth et al. | ................. 73/866.5 |
| 2004/0036043 | A1 | * | 2/2004 | Murshid | ..................... 250/573 |

OTHER PUBLICATIONS

Simpson, J.O. et al., "Fundamental Insight on Developing Low Dielectric Constant Polymides", *NASA Langley Research Center*, Hampton, VA 23681-0001, 19 pages (1997).

* cited by examiner

*Primary Examiner*—Hoa Q Pham
(74) *Attorney, Agent, or Firm*—Smith, Gambrell & Russell LLP

(57) ABSTRACT

Methods and systems are provided for determining the density and/or temperature of a fluid based on a reflection of optical energy directed at the fluid.

36 Claims, 13 Drawing Sheets

SPECIFICATIONS:
1. 2X2 FBT / FUSED (GLASS/GLASS) FIBER OPTIC COUPLER
2. FIBER: 200 um CORE
3. CONNECTORS: 4X SMA-905
4. INSERTION LOSS
   - MANUFACTURES SPECIFICATION: COUPLER ≤ 3.6 dB
   - UNIFORMITY 0.6dB
   - PROVIDE ASSY INSERTION LOSS YEST DATA @850nm PER FOTP-171: ASSY. INSERTION LOSS ≤ 4.1 dB.
   - CONNECTOR LOSS NOT TO EXCEED 0.5 dB
5. DIRECTIVITY< 40dB
6. PACKAGE: MANUFACTURES STANDARD 3mm or BUFFERED FIBER
7. OUTPUT SIDE LEAD LENGTHS TO BE EQUAL WITHIN ±30mm.
8. CONNECTOR POLISH
   - OUTPUT SIDE ≤ 0.5 MICRON
   - INPUT SIDE ≤ 1.0 MICRON.

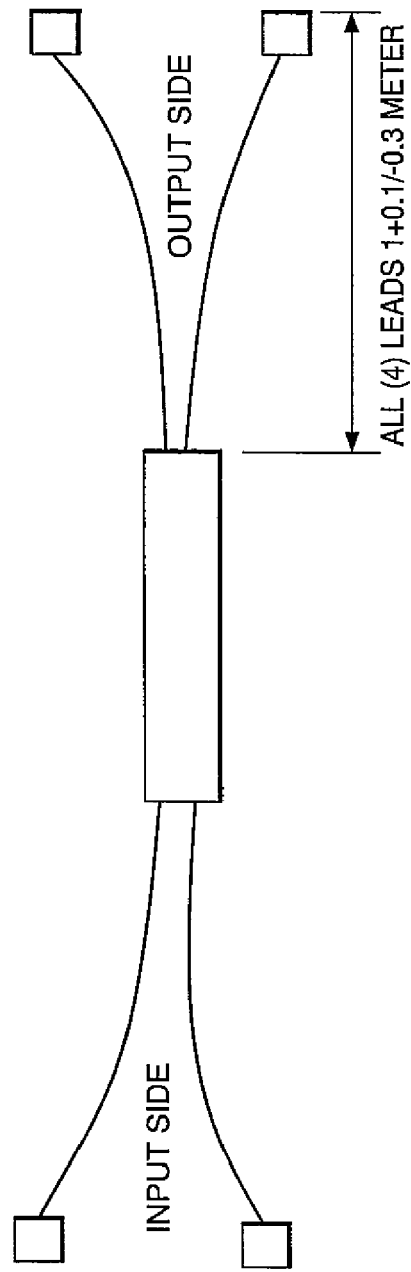

FIG. 8

| Type of Fluid | Measured Index of Refraction | Dielectric Constant (calculated from Maxwell's Indentity) | Measured Density (kg/l) | Output voltage of Light Detector (volts dc) |
|---|---|---|---|---|
| Air | 1.000 | 1.000 |  | 8.122 |
| Water | 1.333 | 1.769 | Out of range of hydrometer | 8.138 |
| Jet A aviation fuel | 1.449 | 2.100 | 0.804 | 4.346 |
| AEROSHELL 41 lubricating oil | 1.473 | 2.170 | 0.876 | 3.225 |
| SAE-10W-30 libricating oil | 1.477 | 2.183 | 0.866 | 3.023 |

FIG. 9

| Measured Temperature of Jet A Fuel Sample (°C) | Known (Published) Value of Density of Jet A Fuel at Measured Temperature | Output voltage of Light Detector (volts dc) | Density of Jet A Fuel Calculated and Displayed by Prototype System (kg/l) (°C) | Temperature of Jet A Fuel Calculated and Displayed Prototype system (°C) |
|---|---|---|---|---|
| -7 | 0.8281 | 3.488 | 0.8277 | -7.9 |
| -5 | 0.8266 | 3.514 | 0.8266 | -6.7 |
| -4 | 0.8259 | 3.534 | 0.8259 | -5.8 |
| -3 | 0.8252 | 3.560 | 0.8252 | -4.6 |
| -2 | 0.8244 | 3.586 | 0.8244 | -3.4 |
| -1 | 0.8237 | 3.610 | 0.8236 | -2.3 |
| 0 | 0.8230 | 3.634 | 0.8228 | -1.2 |
| 2 | 0.8216 | 3.691 | 0.8210 | 1.4 |
| 3 | 0.8208 | 3.715 | 0.8202 | 2.5 |
| 4 | 0.8201 | 3.724 | 0.8200 | 2.9 |
| 5 | 0.8194 | 3.754 | 0.8191 | 4.2 |
| 6 | 0.8187 | 3.774 | 0.8184 | 5.1 |
| 7 | 0.8179 | 3.786 | 0.8180 | 5.7 |
| 8 | 0.8172 | 3.790 | 0.8178 | 5.9 |
| 9 | 0.8165 | 3.821 | 0.8169 | 7.3 |
| 10 | 0.8158 | 3.844 | 0.8162 | 8.3 |
| 11 | 0.8151 | 3.870 | 0.8151 | 9.5 |
| 12 | 0.8143 | 3.892 | 0.8145 | 10.5 |
| 13 | 0.8136 | 3.904 | 0.8141 | 11.1 |
| 14 | 0.8129 | 3.927 | 0.8134 | 12.2 |
| 15 | 0.8122 | 3.946 | 0.8128 | 13.0 |
| 16 | 0.8114 | 3.970 | 0.8120 | 14.1 |
| 17 | 0.8107 | 3.992 | 0.8112 | 15.1 |
| 18 | 0.8100 | 4.013 | 0.8106 | 16.0 |
| 19 | 0.8903 | 4.037 | 0.8098 | 17.1 |
| 20 | 0.8086 | 4.058 | 0.8091 | 18.1 |
| 21 | 0.8078 | 4.088 | 0.8082 | 19.4 |
| 22 | 0.8071 | 4.113 | 0.8074 | 20.6 |
| 23 | 0.8064 | 4.139 | 0.8065 | 21.7 |
| 24 | 0.8057 | 4.159 | 0.8059 | 22.7 |
| 25 | 0.8049 | 4.183 | 0.8051 | 23.7 |
| 26 | 0.8042 | 4.206 | 0.8043 | 24.8 |
| 27 | 0.8035 | 4.231 | 0.8037 | 25.9 |
| 28 | 0.8028 | 4.254 | 0.8030 | 27.0 |
| 29 | 0.8021 | 4.282 | 0.8019 | 28.2 |
| 30 | 0.8013 | 4.302 | 0.8014 | 29.2 |

FIG. 10

METHODS AND SYSTEMS FOR DETERMINING THE DENSITY AND/OR TEMPERATURE OF FLUIDS

CROSS REFERENCE RELATED APPLICATION

This application claims priority under 35 U.S.C. § 119(e) to U.S. provisional application No. 60/782,002, filed Mar. 14, 2006, the contents of which is incorporated by reference herein in its entirety.

TECHNICAL FIELD

The present application relates generally to measuring devices for determining an unknown quantity, and more particularly, to methods and systems for determining the density and/or temperature of a fluid such as aircraft fuel.

BACKGROUND

The weight of a fluid often needs to determined based on the measured level of the fluid in a tank or other container. The fluid weight is often determined by measuring the dielectric constant of the fluid, and calculating the fluid density based on a known relationship between the dielectric constant and density for the particular fluid. The density can be used to calculate the weight of the fluid based on the volume of fluid in the tank. The volume of fluid can be calculated based on the measured fluid level.

The dielectric constant of a fluid is typically measured using an electrical sensor immersed in the fluid. The use of an electrical sensor for this task can present substantial disadvantages. For example, the introduction of electrical current into a tank of fluid can generate an explosion hazard. In particular, the electrical current has the potential to introduce a spark within the tank due to, for example, chaffed insulation on the wiring associated with the dielectric current sensor. A spark can ignite explosive vapors that may be present in the tank.

For example, Jet A fuel used by commercial aircraft has a flash point of about 38° C. Thus, sufficient vapors may be present in a tank of Jet A fuel under normal operating conditions to cause an explosion if a spark is present within the tank.

Electrical sensors are susceptible to signal degradation in the presence of electromagnetic interference. Moreover, electrical sensors, when used to measure fuel levels, can lose accuracy as the amount of water and other contaminants in the fuel increases.

An ongoing need therefore exists for a system that can determine the density of a fluid in a tank or other container without introducing electrical current into the tank or container, and that can function in a satisfactory manner in the presence of contaminates and/or electromagnetic interference.

SUMMARY

Methods and systems are provided for determining the density and/or temperature of a fluid based on a reflection of optical energy directed at the fluid.

Methods comprise illuminating an interface of an optical waveguide and a fluid with optical energy, determining a property of a reflection of the optical energy, and determining a density and/or temperature of the fluid based on the property of the reflection.

Other methods comprise immersing an end of an optical fiber in a fluid, directing optical energy at an interface of the optical fiber and the fluid, and determining a density and/or temperature of the fluid based on an intensity of a reflection of the optical energy from the interface of the optical fiber and the fluid.

Other methods comprise transmitting light to an end of an optical waveguide exposed to a fluid, and calculating a density and/or temperature of the fluid based on a predetermined relationship between a reflection of the light and the density and/or temperature of the fluid.

Embodiments of systems comprise a source of optical energy, a detector of optical energy, an optical waveguide in optical communication with the source of optical energy and the detector of optical energy, and a computing device communicatively coupled to the detector of optical energy. The computing device determines a density and/or temperature of a fluid based on a reflection of the optical energy from an interface of the optical waveguide and the fluid.

BRIEF DESCRIPTION OF THE DRAWINGS

The foregoing summary, as well as the following detailed description of embodiments, are better understood when read in conjunction with the appended diagrammatic drawings. For the purpose of illustrating the embodiments, the drawings diagrammatically depict specific embodiments. The appended claims are not limited, however, to the specific embodiments disclosed in the drawings. In the drawings:

FIG. 8 is a diagrammatic illustration of an optical splitter/combiner, fiber optic cables, and optical probes of the prototype system shown in FIGS. 6 and 7;

FIG. 9 is a table of various fluids used to calibrate the prototype system shown in FIGS. 6-8, and calibration data;

FIG. 10 is a table of calibration data for the prototype system shown in FIGS. 6-8;

DETAILED DESCRIPTION OF ILLUSTRATIVE EMBODIMENTS

Figure 1:
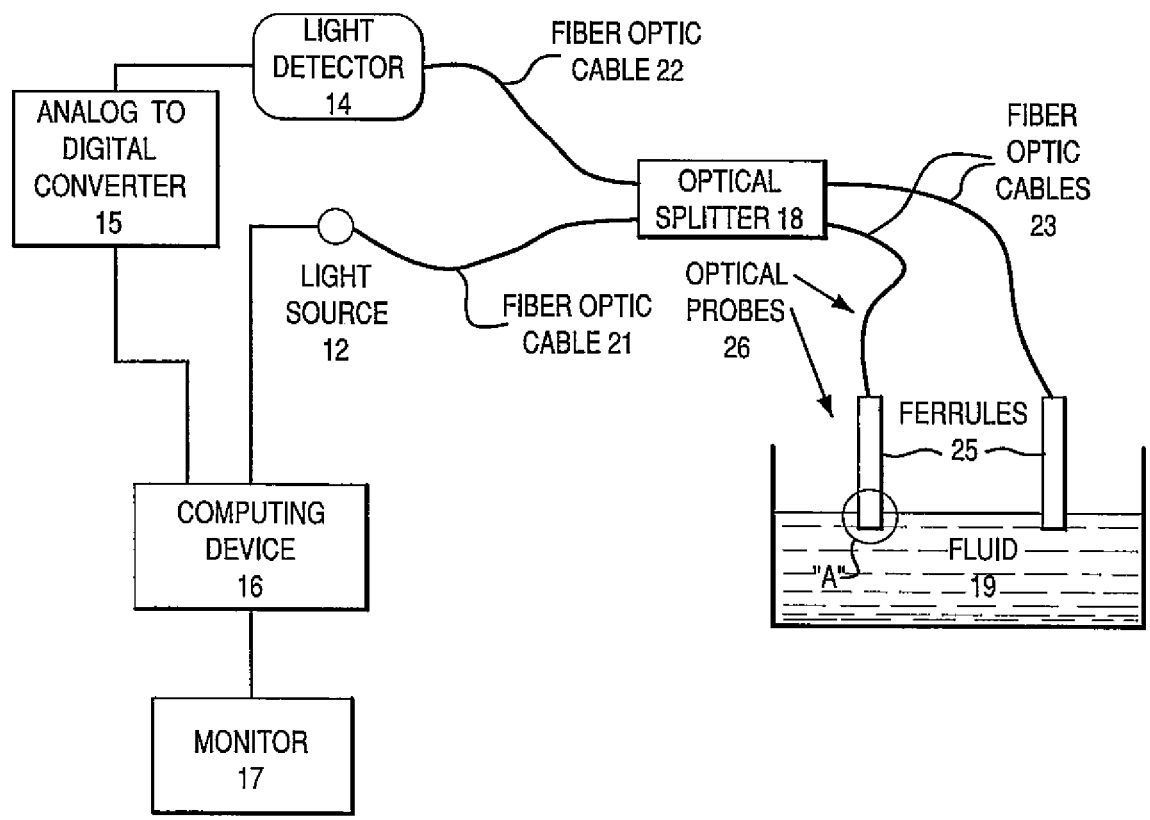
FIG. 1 is a diagrammatic illustration of an embodiment of system for determining the density and/or temperature of a fluid.

An embodiment of a system 10 for determining the density and/or temperature of a fluid is depicted in FIG. 1. The system 10 comprises a source of optical energy in such as a light source 12, a detector of optical energy such as a light detector 14, and an optical splitter/combiner 18. The light detector 14 can be, for example, a photodiode that generates an electrical output proportional to the intensity of optical energy input thereto.

The light source 12 can be selected so that its output has a wavelength the matches the optimal-response wavelength of the light detector 14. Alternatively, the light source 12 can be selected so that its output has a wavelength band that minimizes energy losses in the optical waveguide to which the light source 12 is connected, and in the splitter/combiner 18. The light source 12 can be, for example, a light-emitting diode (LED), such as a green LED, having an output wavelength in the infrared or visible range. Other types of light sources, such as solid-state lasers, gas lasers, dye lasers, and other types of lasers, can be used in the alternative.

The light detector 14 can be, for example, a photodiode that generates an electrical output proportional to the intensity of optical energy input thereto. Other types of detectors of optical energy, such as optical power meters, can be used in the alternative.

The optical splitter/combiner 18 can be, for example, a 3 dB multimode optical splitter/combiner 18. The use of a 3 dB splitter/combiner is specified for exemplary purposes only; other types of splitter/combiners can be used in the alternative. The light source 12 is in optical communication with the splitter/combiner 18 by way of a fiber optic cable 21, as shown in FIG. 1. The light detector 14 is in optical communication with the splitter/combiner 18 by way of a fiber optic cable 22.

The system 10 also comprises two fiber optic probes 26 in optical communication with the splitter/combiner 18. Each probe 26 comprises a ferrule 25 formed from a suitable material such as stainless steel, and a fiber optic cable 23.

Figure 2A:
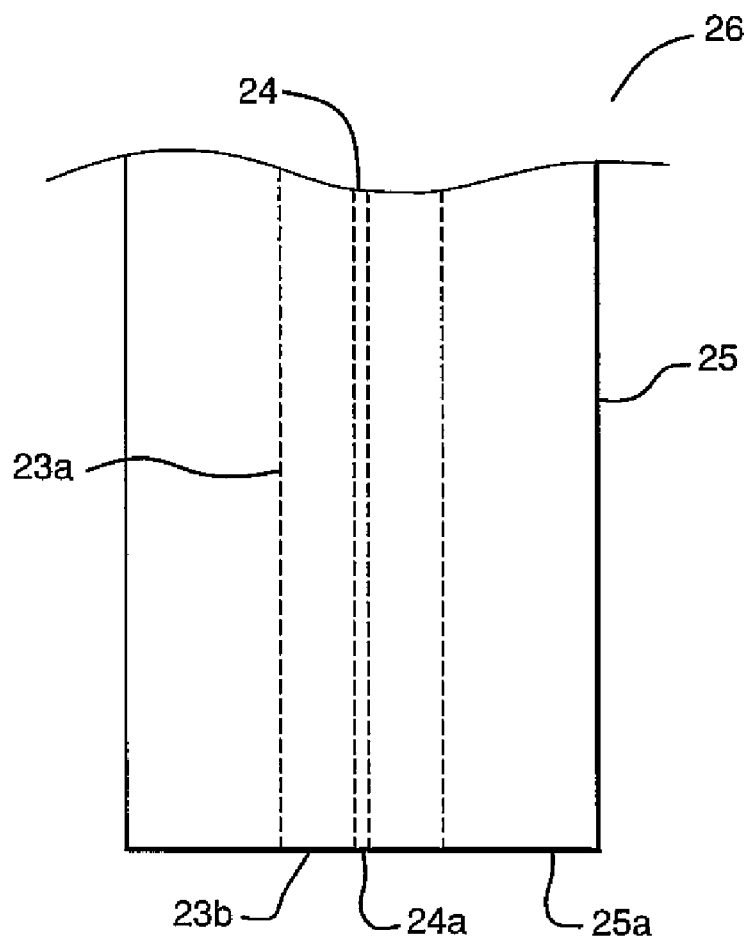
FIG. 2A is a magnified view of the area designated "A" in FIG. 1, depicting a portion of an optical probe of the system shown in FIG. 1.
Figure 2B:
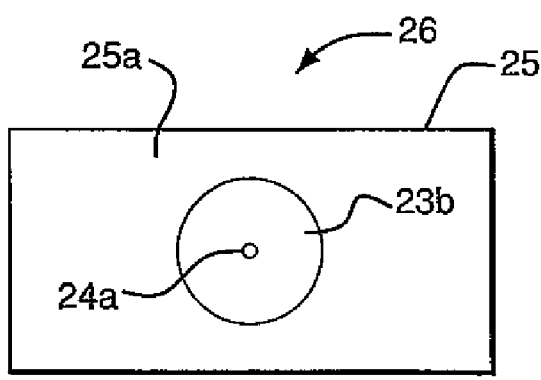
FIG. 2B depicts an end face of the optical probe shown in FIG. 2.

Each fiber optic cable 23 includes a single optical fiber 24 that acts as a waveguide. The optical fiber 24 associated with one of the fiber optic cables 23 is depicted in FIGS. 2A and 2B. The optical fibers 24 are formed from glass; optical fibers formed from materials other than glass can be used in the alternative. Fiber optic cables comprising multiple optical fibers can be used in lieu of single-fiber cables if necessary or otherwise desired, to increase the intensity of the light transmitted between the light source 12 and the light detector 14. One, or more than two of the optical probes 20 can be used in alternative embodiments.

An end portion 23a of each fiber optic cable 23 is housed within an associated one of the ferrules 25, as shown in FIG. 2A. An end 23b of the fiber optic cable 23 is cleaved so that the end 23b lies substantially flush with an end face 25a of the ferrule 25, and an end 24a of the enclosed optical fiber 24 is exposed as shown in FIG. 2B. The end 24a of the optical fiber 24 can be polished by a suitable technique such as lapping.

The system 10 further comprises an analog to digital (A/D) converter 15 communicatively coupled to the light detector 14, as shown in FIG. 1. The system 10 also comprises a computing device 16. The computing device 16 is communicatively coupled to the A/D converter 15 and the light source 12. The A/D converter 15 can be integrated with the light detector 14 or the computing device 16 in alternative embodiments.

The computing device 16 can be communicatively coupled to the light source 12, so that the computing device 16 can activate and deactivate the light source 12. Alternative embodiments can be configured so that the light source 12 is not communicatively coupled to the computing device 16, and is not activated or deactivated by the computing device 16.

Figure 3:
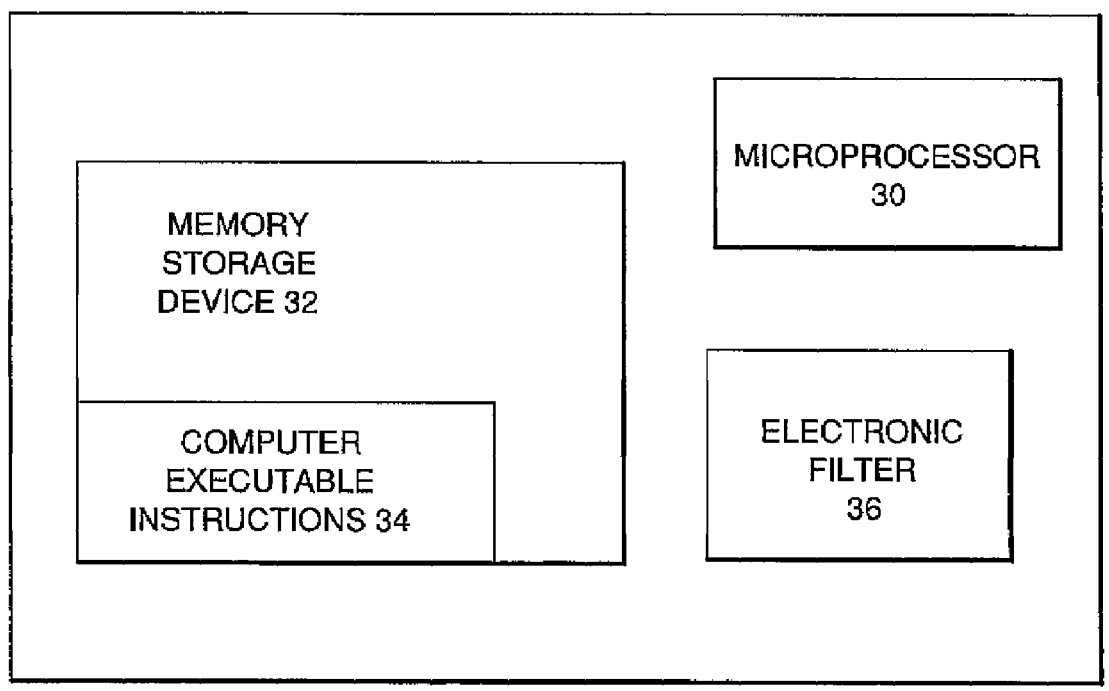
FIG. 3 is a block diagram of a computing device of the system shown in FIGS. 1-2B.

The computing device 16 can include a processor such as a microprocessor 30, as shown in FIG. 3. The computing device 16 can also include a non-volatile memory-storage device 32, such as flash memory or read only memory, communicatively coupled to the microprocessor 30. The computing device 16 can further include a set of computer executable instructions 34 stored on the memory-storage device 32. The computing device 16 can also include an electronic filter 36 communicatively coupled to the microprocessor 30.

The system 10 can also include a display, such as a monitor 17, communicatively coupled to the computing device 16 as shown in FIG. 1. The display 17 can be integrated with the computing device 16 in alternative embodiments.

During operation of the system 10, the end face 25a of each ferrule 25 is immersed in a fluid 19 as shown in FIG. 1, so that the end 24a of the associated optical fiber 24 is exposed to the fluid 19. The fluid 19 can be, for example Jet A fuel.

Optical energy in the form of light generated by the light source 12 is transmitted to the end 24a of the optical fiber 24 of each fiber optic cable 23 by way of the fiber optic cable 21 and the splitter/combiner 18.

The fluid 19 and the optical fibers 24 have different indexes of refraction. For example, the index of refraction of the glass optical fibers 24 is about 1.56. The index of refraction for Jet A fuel is about 2.04 when the temperature of the fuel is 80° C., and about 2.21 when the temperature of the fuel is about −40° C.

A Fresnel reflection is generated when light is incident upon the interface of two materials having different indexes of refraction. The light generated by the light source 12 thus generates Fresnel reflections when the light is incident upon the interface of each optical fiber 24 and the fluid 19. The reflected light is transmitted to the splitter/combiner 18 by the fiber optic cables 23, combined by the splitter/combiner 18, and transmitted to the light detector 14 by the fiber optic cable 22. The light detector 14 generates an electrical output proportional to the intensity of the reflected light that reaches the light detector 14. As discussed above, detectors of optical energy other than light detectors can be used in alternative embodiments. In applications where an optical power meter is used as the detector of optical energy, the intensity of the reflected light can be measured directly, i.e., without being converted to an electrical current as in the light detector 14.

The intensity of the reflected light as registered by the light detector 14 can be used to determine the density and temperature of the fluid 19, as follows.

The dielectric constant of a fluid such as Jet A fuel varies with the temperature of the fluid. The index of refraction Jet A fuel is related to dielectric constant of the fuel by Maxwell's identity, as expressed in the following equation:

$$n_{(\varepsilon_r)} = \sqrt{\varepsilon_r} \qquad (1)$$

where n and $\varepsilon_r$ represent the index of refraction and the dielectric constant, respectively.

The Fresnel reflection coefficient represents the intensity of the optical energy reflected due to the Fresnel reflection that occurs at the interface of two materials of different indexes of refraction, per unit intensity of the optical energy incident upon the interface. When optical energy such as light is at near-normal incidence to the interface between two materials of different refractive indexes, such as a glass optical fiber and a fluid such as Jet A fuel and a glass optical fiber, the intensity of the resulting Fresnel reflection can be calculated as follows:

$$R_s = \left(\frac{n_g - n_m}{n_g + n_m}\right)^2 \qquad (2)$$

where Rs is the Fresnel reflection coefficient, nm is the index of refraction of the fluid, and $n_g$ is the index of refraction of the optical fiber.

Equation (2) can be modified as follows using the relationship between the dielectric constant and index of refraction obtained from Maxwell's identity, so that the Fresnel reflection coefficient can be calculated based on the dielectric constant of the fluid.

$$R_{S_{(\varepsilon_r)}} = 10\log_{10}\left[\left(\frac{n_g - \sqrt{\varepsilon_r}}{n_g + \sqrt{\varepsilon_r}}\right)^2\right] \qquad (3)$$

The dielectric constant of Jet A fuel varies with the temperature of the fuel, as noted above. The Fresnel reflection coefficient generated at the interface of Jet A fuel and another material having a different refractive index therefore varies with the temperature of the fuel.

The range throughout which the Fresnel reflection coefficient varies in response to changes in the temperature of the Jet A fuel may be relatively large. The Fresnel reflection coefficient as calculated in equation (3) is therefore expressed decibels, to permit a meaningful comparison of the intensity levels at different fuel temperatures.

Figure 4:
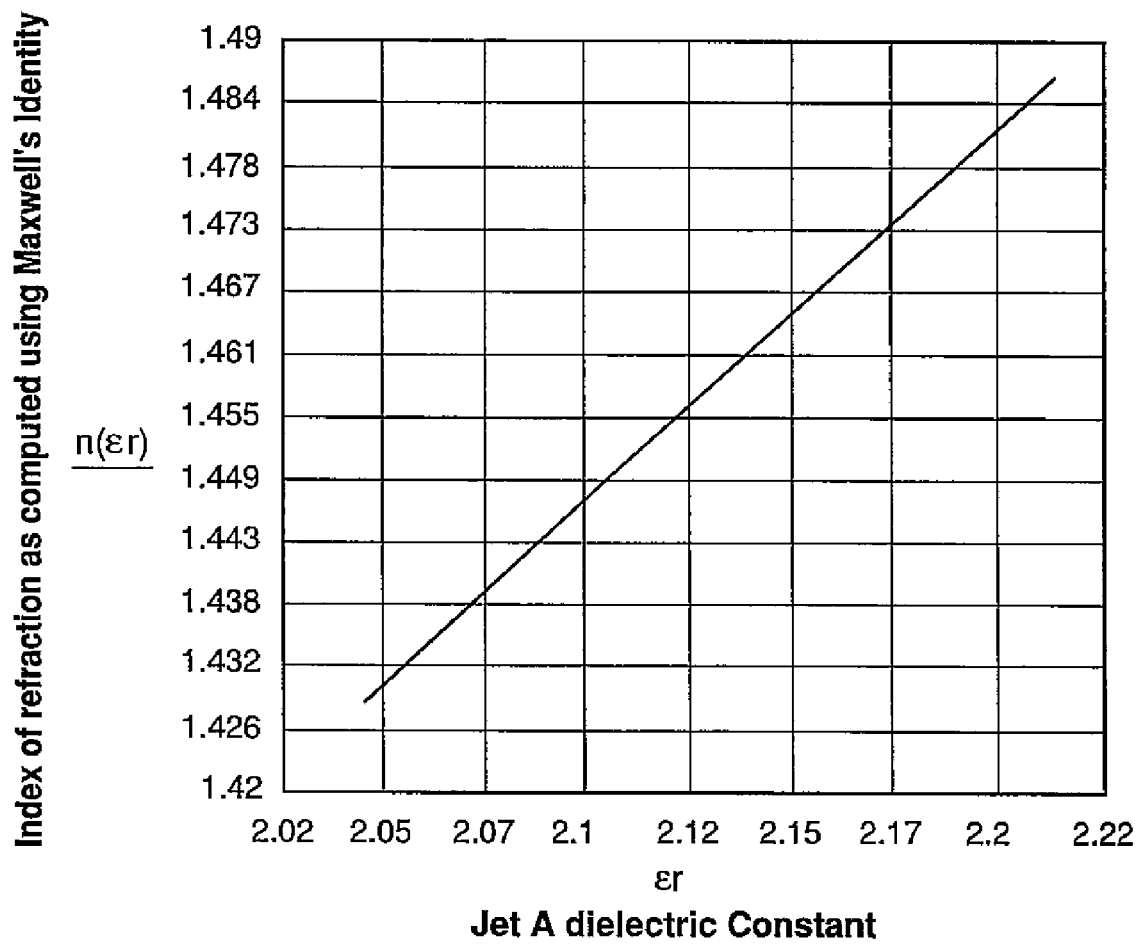
FIG. 4 is a graphical representation of the relationship between the index of refraction and the dielectric constant of Jet A fuel.

FIG. 4 is a graphical representation of the relationship between the index of refraction and the dielectric constant of Jet A fuel. FIG. 4 was generated using the relationship between the index of refraction and dielectric constant provided by Maxwell's identity, i.e., equation (1) above, and published values for the dielectric constant of Jet A fuel.

Figure 5:
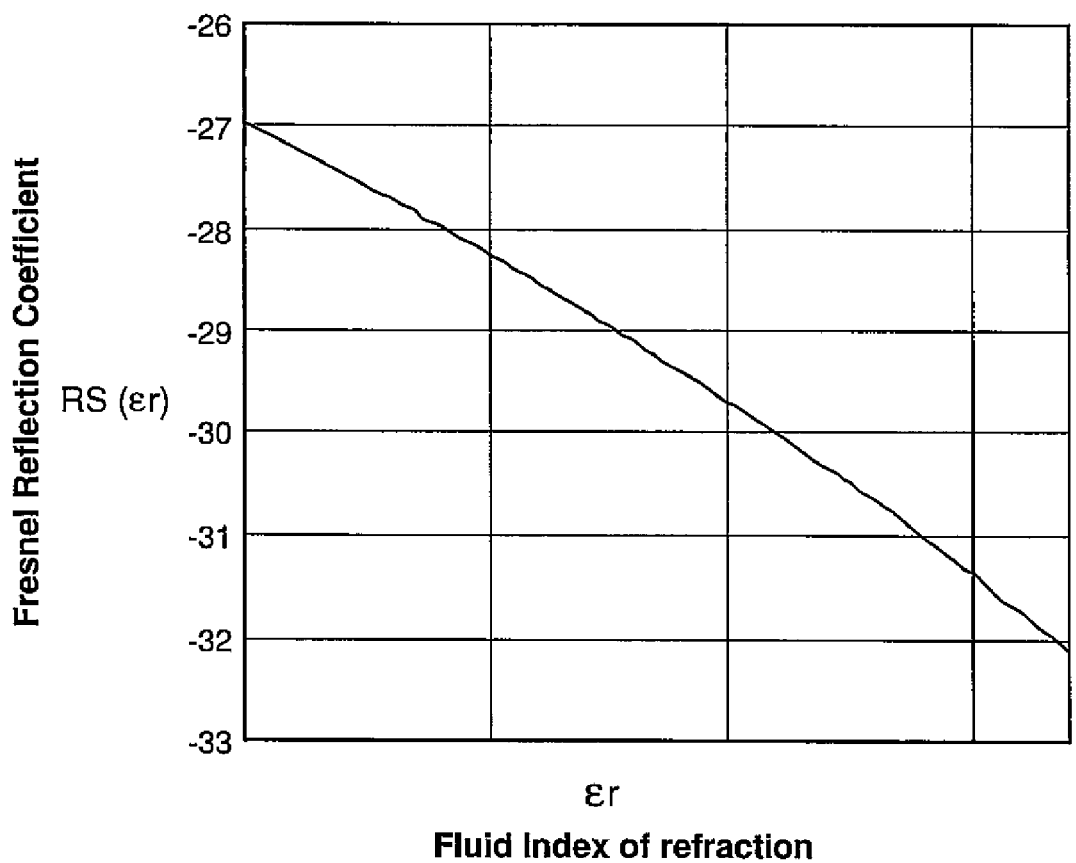
FIG. 5 is a graphical illustration of a calculated relationship between an index of refraction of Jet A fuel at temperatures ranging from −40° C. to 80° C., and an intensity of a reflection of optical energy from an interface of the Jet A fuel and an optical fiber.

The x, or horizontal, axis of FIG. 4 represents the published values of the dielectric constant of Jet A fuel over a range of temperatures. At −40° C., the dielectric constant of Jet A fuel is about 2.21; at 80° C., the dielectric constant of is about 2.04. Applying these values of dielectric constant to equation (3), and using the dielectric constant for an optical waveguide formed from glass, i.e., 1.56, allows the Fresnel reflection coefficient generated at the interface of Jet A fuel and a glass optical fiber to be calculated over the noted temperature range. FIG. 5 is a graphical representation of the calculated Fresnel reflection coefficient as a function of the dielectric constant of Jet A fuel, over a range of fuel temperatures between −40° C. and 80° C.

As shown in FIG. 5, the calculated value of the Fresnel reflection coefficient is about −27.11 dB when the index of refraction and temperature of the Jet A fuel are 2.04 and 80° C., respectively; and about −31.81 dB when the index of refraction and temperature of the fuel are 2.21 and −40° C. The calculated value of the Fresnel reflection coefficient thus changes by about 4.70 dB when the fuel temperature varies between 80° C. and −40° C. The magnitude of this change is believed to be sufficient to allow the intensities of the Fresnel reflections generated at different fuel temperatures to be distinguished using commercially-available equipment.

A correlation can be generated between the Fresnel reflection coefficient and the fuel temperature by documenting the response of the light detector 14 to the Fresnel reflections generated at a series of known fuel temperatures. The Fresnel reflection coefficient represents the intensity of the optical energy reflected due to the Fresnel reflection that occurs at the interface of two materials of different indexes of refraction, per unit intensity of the optical energy incident upon the interface. The correlation between the Fresnel reflection coefficient and the temperature of Jet A fuel can therefore be used to determine the temperature of the fuel based on the intensity the Fresnel reflection measured by the light detector 14. The density of the fuel, in turn, can be found based on the known relationship between the density and temperature of Jet A fuel.

A system for determining the density and temperature of a fluid in the above-noted manner was constructed by Applicants. The system was used to determine the density and temperature of Jet A fuel as follows. This system is depicted in FIGS. 6 through 8, and is hereafter referred to as "the prototype system."

The prototype system included a Nichia Corporation NSPG500S green LED as a light source. The light source was driven at 23.2 mA DC.

Figure 7:
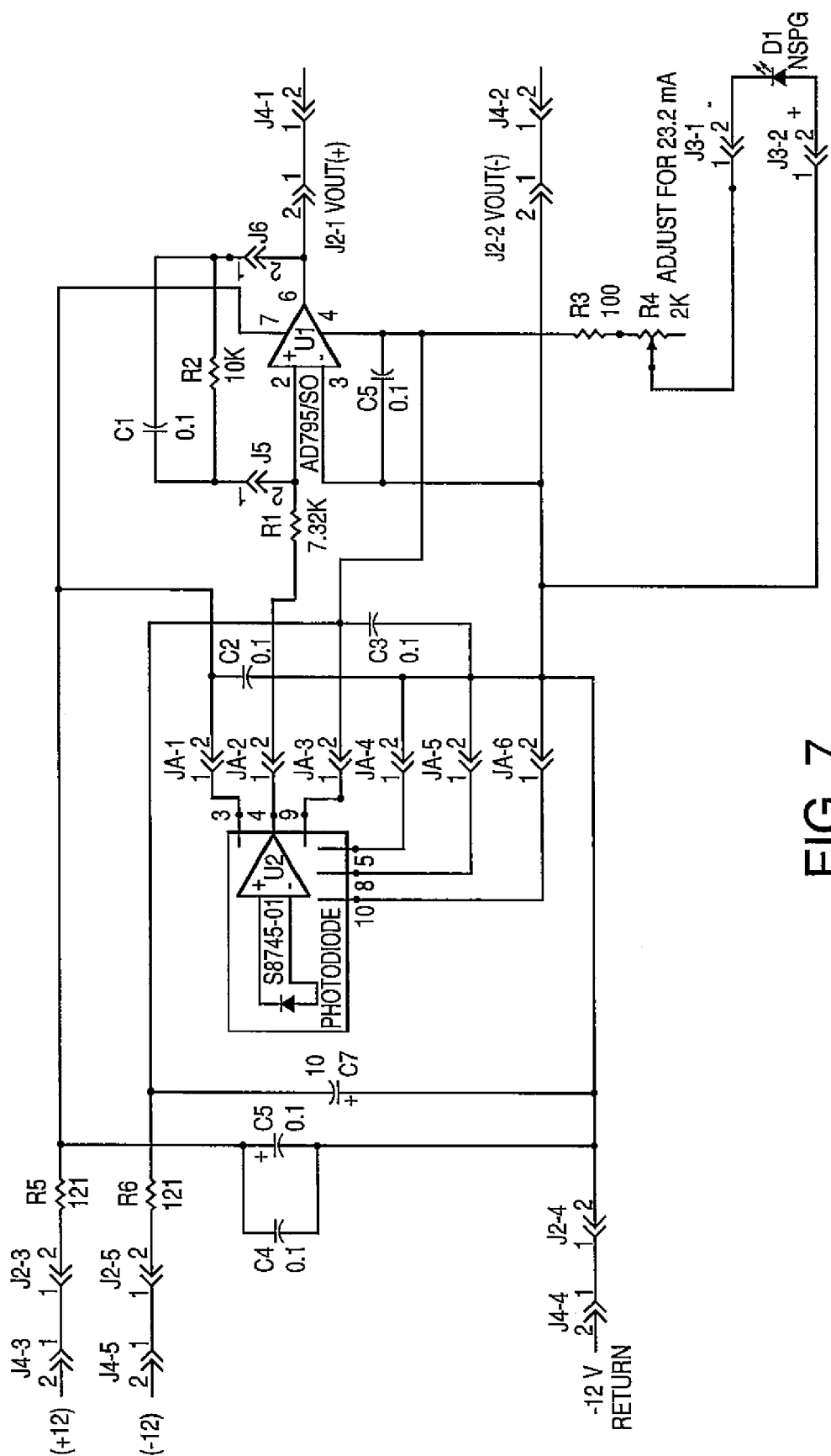
FIG. 7 is a schematic illustration of a light detector of the prototype system shown in FIG. 6.

The light detector depicted in FIG. 7 was used in the prototype system. The light detector comprises a photodiode which includes a field effect transistor (FET) amplifier, designated "U2" in FIG. 7. The light detector was operated with a reduced gain of 1.37, as set by the resistor values R1 and R2. The values of R1 and R2 denoted in FIG. 7 were chosen to provide the light detector with a suitable span of output voltages, i.e., about 2.0 volts, based on the intensity of the optical energy incident upon the photodiode.

Figure 6:
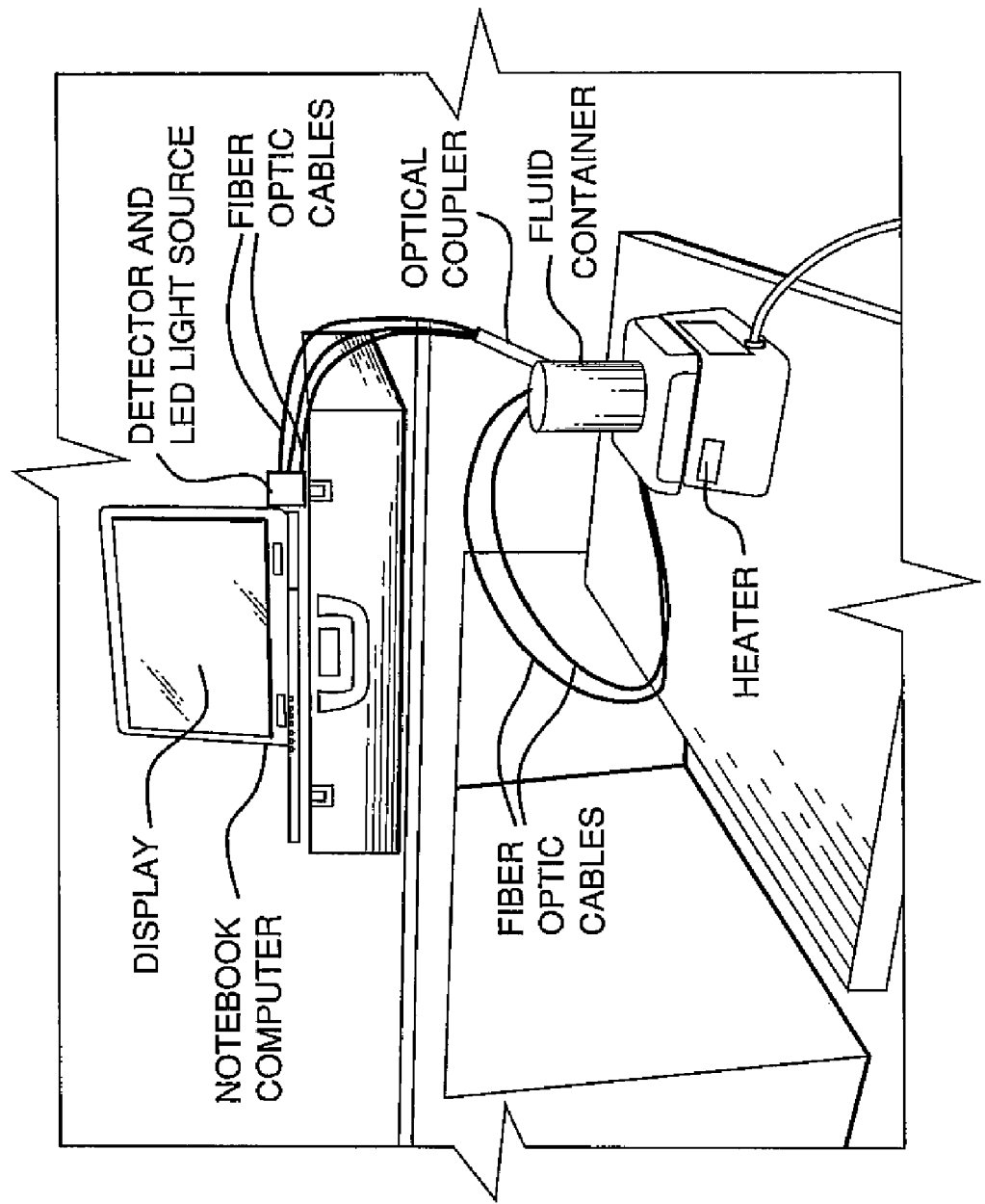
FIG. 6 depicts a prototype system for determining the density and/or temperature of a fluid.

The photodiode also includes a buffer amplifier, designated "U1" in FIG. 6, and a filter circuit comprising the circuit elements designated "R1," "R2," "C2," and "C5."

The prototype system also included a FONT Canada FMMC-200-SMA-AL optical splitter/combiner, with optical probes and fiber optic cables. Specifications of the splitter/combiner are listed in FIG. 8. A 16-bit A/D converter (not shown) was used to digitize the output voltage across the terminals "J4-1" and "J4-2" of the light detector.

The prototype system also included a Dell INSPIRON 9300 notebook computer, which was used as a computing device and a monitor. The notebook computer was equipped with a $4^{th}$ order Butterworth polynomial low-pass filter with a cutoff frequency of about 1 Hz. The output of the A/D converter was sampled by the notebook computer, filtered, processed, and then displayed on the display screen of the notebook computer.

The response of the light detector of the prototype system to Fresnel reflections generated by various types of fluids was initially determined. This procedure was conducted to predict the range of output voltages over which the light detector would operate when used to determine the temperature and density of Jet A fuel. The fluids used in the procedure are listed in the table included as FIG. 9, and included water, Jet A fuel, AEROSHELL 41 lubricating oil, SAE 10W-030 lubricating oil, and air.

The index of refraction and the density of each fluid were measured using a model no. 30GS Refractometer from Mettler Toledo International Inc., and a model no. 11-51031 hydrometer from Fisher Scientific International Inc., respectively. The measured values of the index of refraction and density are listed FIG. 9.

The Fresnel reflections were generated by immersing the end faces of the probes of the prototype system in the fluid, and activating the LED light source to produce optical energy of a predetermined intensity and wavelength, i.e., about 0.860 mW at a center wavelength of about 523 nm. The optical energy was transmitted to the fluid interface by way of the various components of the splitter/combiner. The fluids were at room temperature during this procedure.

The output voltage of the light detector of the prototype system in response to the Fresnel reflections associated with each type of fluid was measured using a voltmeter. The resulting output voltages are presented in FIG. 9. The output voltage of the light detector ranged from about 8.138 for water, with an index of refraction of about 1.333, to about 3.023 for SAE 10W-30 oil, with an index of refraction of about 1.477.

The prototype system was subsequently calibrated for use with Jet A fuel. In particular, each probe of the prototype system was partially immersed in a volume of Jet A fuel chilled to a temperature of about −7° C. Fresnel reflections from the interface of the fluid interface and the optical fibers of the optical probes were generated by energizing the LED light source. The output voltage of the light detector in response to the Fresnel reflections was measured using a voltmeter.

The temperature of the Jet A fuel was increased incrementally as shown in FIG. 10, from about −7° C. to about 30° C. The temperature increases were effectuated by a heater on which the container holding the volume of fuel was placed. A calibrated commercial thermometer, i.e., a Fisher model 15-160-30 thermometer, was used to measure the fuel temperature during this procedure.

The output voltage of the light detector of the prototype system to the Fresnel reflections generated at each incremental temperature was documented. A curve fit of the output voltage as a function of temperature was generated. Another curve fit was generated based on the output voltage of the light detector as a function of temperature, and the known relationship between the temperature and density of Jet A fuel. The curve fits were programmed into the notebook computer so that the notebook computer would calculate and display temperature and density readings based on the digitized output of the light detector.

The curve fit for determining the temperature of Jet A fuel based on the output voltage of the light detector of the prototype system, for a range of output voltages from about 2.78 volts to about 5.64 volts, was as follows:

$$\text{temperature (° C.)} = 45.4833 \cdot (\text{output voltage of light detector}) + 165.511 \quad (4)$$

The curve fit for determining the density of Jet A fuel based on the output voltage of the light detector of the prototype system, and the known relationship between the temperature and density of Jet A fuel, for a range of output voltages from about 2.78 volts to about 5.64 volts, was as follows:

$$\text{density (kg/l)} = -0.0323 \cdot (\text{output voltage of light detector}) + 0.9403 \quad (5)$$

The density and temperature of Jet A fuel were subsequently determined over a range of temperatures from about −7° C. to about 30° C. using the prototype system. In particular, the optical probes of the prototype system were partially immersed in a chilled volume of Jet A fuel. The LED light source of the prototype system was energized to produce optical energy having the previously-noted intensity of about 0.860 mW.

The light detector received the optical energy associated with the resulting Fresnel reflections from the interface of the Jet A fuel and each optical fiber of the optical probes. The responsive output of the light detector was digitized, and input to the notebook computer. The notebook computer calculated and displayed temperature and density readings for the Jet A fuel based on the curve fits represented by equations (4) and (5).

The temperature of the Jet A fuel was increased in increments of about 1° C. by heating the container holding the fuel. The temperature of the fuel was measured at each incremental temperature using the calibrated commercial thermometer, to provide a baseline against which the temperature and density readings produced by the prototype system could be evaluated.

Figure 11:
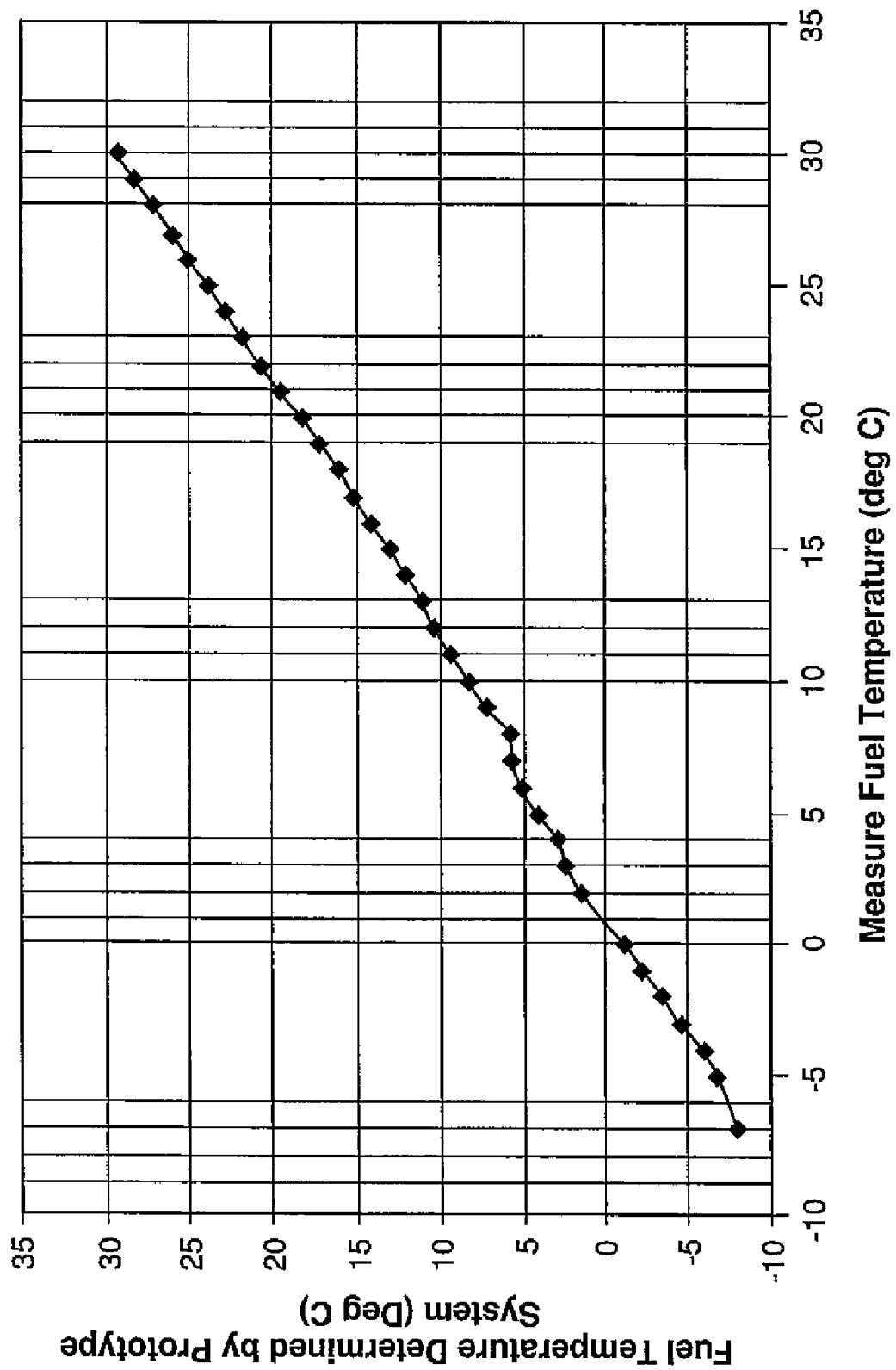
FIGS. 11 and 12 are graphical illustrations of calibration data for the prototype system shown in FIGS. 6-8.
Figure 12:
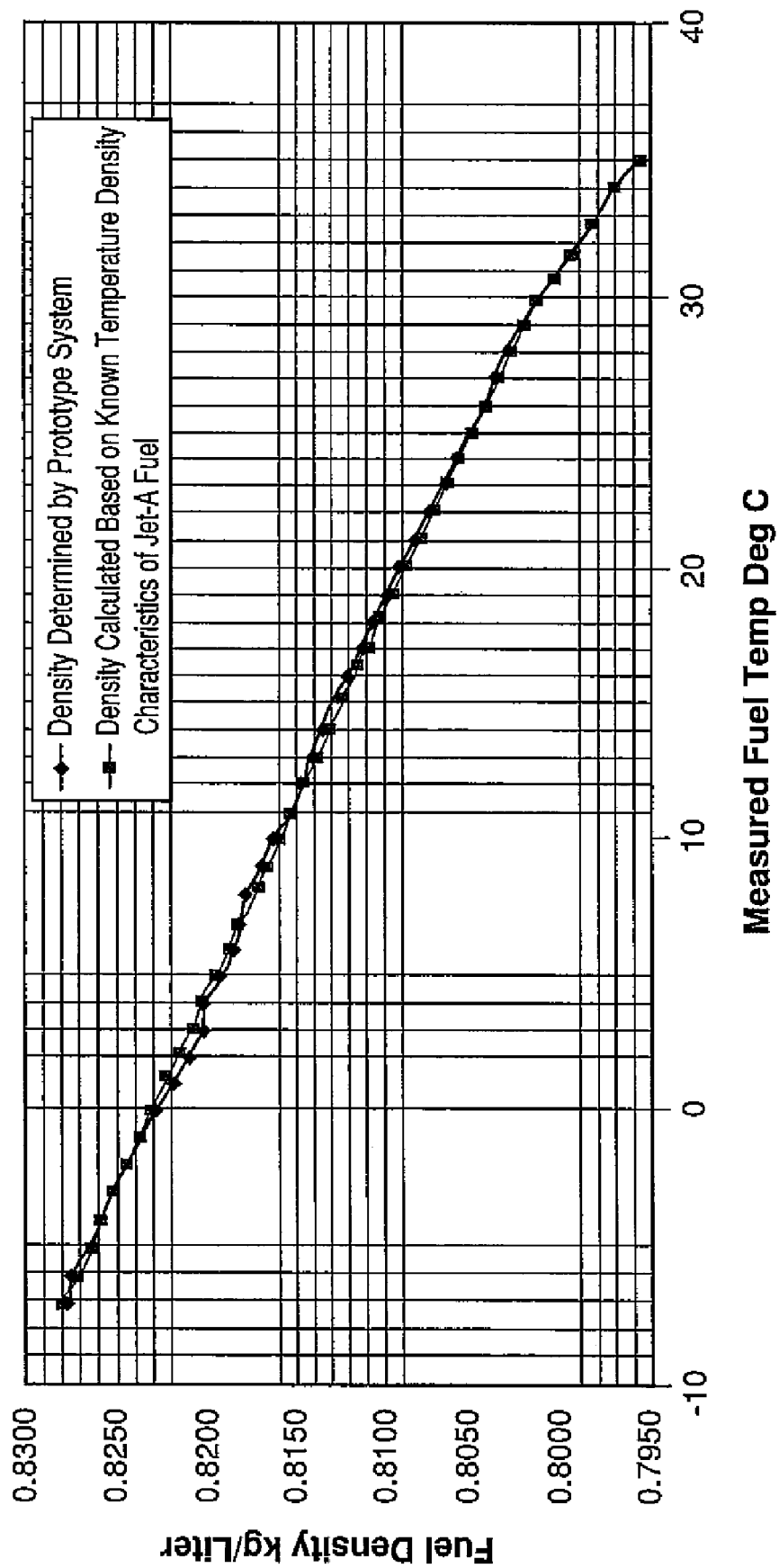

The temperature and density readings produced by the prototype system are presented in tabular form in FIG. 9, and in graphical form in FIGS. 11 and 12. The temperature readings determined using the prototype system compared favorably with the corresponding temperatures measured using the calibrated commercial thermometer. In particular, the temperature readings determined using the prototype system were within about 2° C. of the corresponding measured temperatures.

The density readings determined using the prototype system likewise compared favorably with the corresponding values calculated using the measured temperature, and the predetermined relationship between density and temperature for Jet A fuel. In particular, the density readings determined using the prototype system were within about 0.006 kg/l of the density readings calculated based on the measured temperatures.

The system 10 can thus be used to provide temperature and density measurements for certain types of fluids based on changes in the index of refraction of the fluid. The system 10 operates without introducing electrical current into the fluid itself, or into the tank or container that holds the fluid. The system 10 therefore does not introduce the potential for an explosion caused by the presence of a spark in or near the fluid, in contradistinction to electrical sensors used to measure dielectric constant. The system 10 can thus be used to determine the density and/or temperature of volatile, flammable fluids, such as Jet A fuel, held within an enclosed volume, such as an aircraft fuel tank, without introducing the potential to ignite flammable vapors of the fluid that may be present within the enclosed volume.

Moreover, the optical signals within the system 10 are not subject to degradation due to electromagnetic interference, in contradistinction to electrical sensors. Also, the system 10 does not include moving parts that can wear, jam, or otherwise degrade the reliability or maintainability of the system 10.

The foregoing description is provided for the purpose of explanation and is not to be construed as limiting. While the embodiments have been described with reference to specific embodiments or methods, it is understood that the words which have been used herein are words of description and illustration, rather than words of limitation. Furthermore, although particular embodiments and methods have been described herein, the appended claims are not intended to be limited to the particulars disclosed herein. Those skilled in the relevant art, having the benefit of the teachings of this specification, may effect numerous modifications to the embodiments and methods as described herein, and changes may be made without departing from the scope of the appended claims.

For example, although the prototype system described herein was used to measure the temperature and density of Jet A fuel, the principles presented herein can be applied to systems and methods for determining density, temperature, and/or refractive index of any type of fluid whose index of refraction undergoes a measurable change over the temperature range of interest.

Figure 13A:
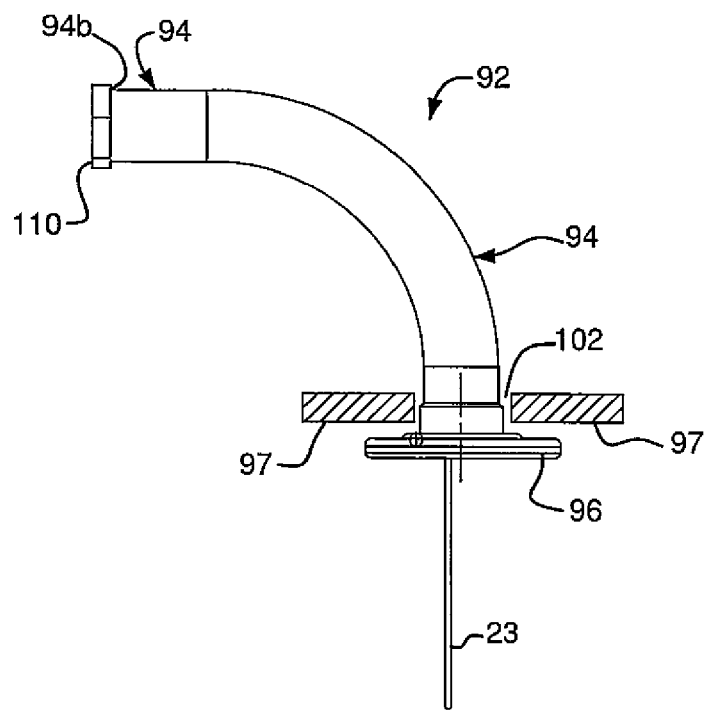
FIGS. 13A-13C are a side view, a cross-sectional side view, and a bottom perspective view, respectively, of an alternative mounting arrangement for the fiber optic cables of the system shown in FIGS. 1-3.
Figure 13B:
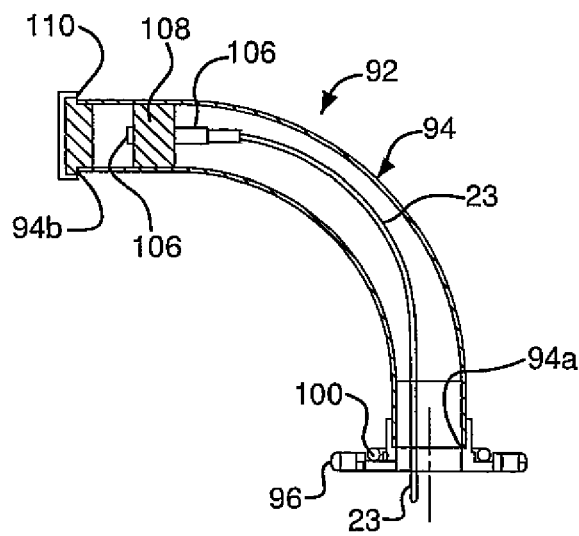
Figure 13C:
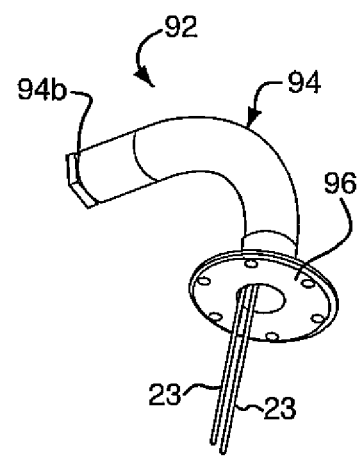

FIGS. 13A-13C depict an alternative mounting arrangement for the ends of the fiber optic cables 23. In particular, FIGS. 13A-13C depict a mount 92 comprising a tube member 94 and a flange 96. The flange 96 is secured to an exterior surface of a bottom wall 97 of a tank or other container that holds a fluid such as the fluid 19. Alternatively, the flange 96 can be secured to an interior surface of the bottom wall 97, or to an interior or exterior surface of another wall of the container. The flange 96 can include an O-ring seal 100 that seals the interface between the flange 96 and the tank 98.

A first end 94a of the tube member 94 is secured to the flange 96 by a suitable means such as a press fit. The tube member 94 and the flange 96 can be unitarily formed in alternative embodiments. A through hole 102 is formed in the wall 97, as shown in FIG. 13A, to accommodate the flange 96 and the tube member 94.

The tube member 94 can be bent by about ninety degrees, so that a second end 94b of the tube member 94 faces a direction substantially perpendicular to the surface of the fluid 19 in the tank when the flange 96 is mounted on the bottom wall 97.

The fiber optic cables 23 extend into the tube member 94. The end of each fiber optic cable 23 is housed in an associated ferrule 106. The ferrules 106 are supported in a plug 108 securely positioned within the tube member 94, proximate the second end 94b thereof, so that the end faces 24a of the optical fibers 24 are exposed to the interior of the tank. The plug 108 acts as a seal that prevents leakage of the fluid 19 from the tank by way of the tube member 94.

A filter 110 is mounted on the second end 94b of the tube member 94. The filter 94 can be, for example, a fine mesh screen that permits the fluid 19 to enter the tube member 94 by way of the second end 94b, so that the fluid 19 immerses the ends faces 24a of the optical fibers 24.

What is claimed:

1. A method, comprising:
    illuminating an interface of an optical waveguide assembly and a fluid with optical energy;
    determining a property of a reflection of the optical energy; and
    determining a density and/or temperature of the fluid based on the property of the reflection, wherein determining a density and/or temperature of the fluid based on the property of the reflection comprises relating the density and/or temperature of the fluid to the property of the reflection based on a predetermined relationship between the density and/or temperature of the fluid and the property of the reflection, and wherein the optical waveguide assembly comprises a splitter/combiner and a pair of fiber optical probes in optical communication with the splitter/combiner, with said probes comprising a fiber optic cable and a supporting ferrule and each fiber optic cable comprises at least one interior optical fiber surrounded by an additional component of said fiber optic cable, and said optical waveguide assembly further comprising a mount that includes a tubular conduit, and said optical probes being fixedly mounted in fluid sealed fashion at an end region of said mount such that each fiber optic cable is exposed to define the interface with the fluid, and wherein the method further includes immersing an end of the optical probes in the fluid such that an exposed end of each optical fiber is fixed in position at a location where said ends are placed in contact with the fluid.

2. The method of claim 1, wherein illuminating an interface of an optical waveguide assembly and a fluid with optical energy comprises transmitting the optical energy from a source of optical energy to the interface of the optical waveguide assembly and the fluid, and wherein the exposed fiber optic cable includes exposed fiber optic cable ends positioned flush with respect to a ferrule surface.

3. The method of claim 2, wherein transmitting the optical energy from a source of optical energy to the interface of the optical waveguide assembly and the fluid comprises transmitting the optical energy from a green light-emitting diode LED to the interface of the optical waveguide and the fluid.

4. The method of claim 2, wherein each fiber optic cable includes a single optical fiber acting as a waveguide in communication with the source of optical energy.

5. The method of claim 1, wherein the property of the reflection is an intensity of the reflection.

6. The method of claim 5, wherein determining a density and/or temperature of the fluid based on the property of the reflection comprises measuring the intensity of the reflection.

7. The method of claim 6, wherein measuring the intensity of the reflection comprises measuring the intensity of the reflection using a detector of optical energy.

8. The method of claim 7, wherein measuring the intensity of the reflection using a detector of optical energy comprises measuring the intensity of the reflection using a photodiode.

9. The method of claim 1, further comprising transmitting the optical energy and the reflection of the optical energy through a multimode optical splitter/combiner.

10. The method of claim 1, wherein the reflection of the optical energy is a reflection of the optical energy from an interface of the waveguide and the fluid.

11. The method of claim 1, wherein immersing the exposed ends of the optical probes in the fluid comprises immersing a cleaved and polished end of each optical fiber in the fluid.

12. The method of claim 1, wherein:
    illuminating an interface of an optical waveguide assembly and a fluid with optical energy comprises illuminating an interface of the optical waveguide assembly and Jet A fuel with optical energy; and
    determining a density and/or temperature of the fluid based on the property of the reflection comprises determining a density and/or temperature of the Jet A fuel based on the property of the reflection.

13. The method of claim 12, further comprising an optical energy detector and a computing device and wherein the computing device determines a density and/or temperature of Jet A fuel based on a reflection of the optical energy from an interface of the optical waveguide and the Jet A fuel based on a respective one of formulas (a) and (b):
    (a) density (kg/l)=−0.0323·(output voltage of the optical energy detector)+0.9403
    (b) temperature (°C.)=45.4833·(output voltage of the optical energy detector)+165.511.

14. The method of claim 1, wherein said tubular conduit has a first end fixed in position to a vessel containing the fluid and wherein the probes are fixed in position within a fluid access end of said tubular conduit with a sealing plug provided at the fluid access end region of said tubular conduit and wherein interfacing the optical fibers with the fluid includes fixing in position the interface of each optical fiber between the filter and said sealing plug relative to fluid flow in said tubular conduit.

15. A system, comprising:
a source of optical energy;
a detector of optical energy;
an optical waveguide assembly in optical communication with the source of optical energy and the detector of optical energy; and
a computing device communicatively coupled to the detector of optical energy, wherein the computing device determines a density and/or temperature of a fluid based on a reflection of the optical energy from an interface of the optical waveguide assembly and the fluid, and wherein the optical waveguide assembly comprises a splitter/combiner and a pair of fiber optic probes in optical communication with the splitter/combiner, with said probes comprising a fiber optic cable and a supporting ferrule, and each fiber optic cable comprises at least one interior optic fiber surrounded by an additional component of said fiber optic cable, and said optical waveguide assembly further comprising a mount that includes a tubular conduit and said probes being fixedly mounted in fluid sealed fashion at an open, fluid contact end region of said mount such that each optic fiber is exposed to define the interface with the fluid.

16. The system of claim 15, wherein the source of optical energy is a light source.

17. The system of claim 16, wherein the light source is a green light-emitting diode.

18. The system of claim 15, wherein the detector of optical energy is a light detector.

19. The system of claim 18, wherein the light detector is a photodiode.

20. The system of claim 15, wherein the exposed fiber optic cables of said optical waveguide assembly have exposed fiber optic cable ends positioned flush with a surface of said ferrule.

21. The system of claim 15, wherein the optical splitter/combiner is a 3 dB optical splitter/combiner.

22. The system of claim 15, wherein the computing device comprises a processor, and a memory-storage device communicatively coupled to the processor.

23. The system of claim 22, wherein the processor is a microprocessor.

24. The system of claim 22, wherein the memory-storage device is a flash memory or a read only memory.

25. The system of claim 22, wherein the computing device further comprises an electronic filter communicatively coupled to the processor.

26. The system of claim 15, wherein the ferrule of each probe encases the at least one additional component of said fiber optic cable, which in turn encases a respective one of the interior optic fibers, and wherein the additional component, interior optic fiber and ferrule all define a common fluid contact exposed face of said respective probes.

27. The system of claim 15, wherein there is only a single optic fiber in each probe that is in communication with the source of optical energy.

28. The system of claim 15, wherein the computing device determines a density and/or temperature of Jet A fuel based on a reflection of the optical energy from an interface of the optical waveguide and the Jet A fuel based on a respective one of formulas (a) and (b):
(a) density (kg/l)=−0.0323·(output voltage of the optical energy detector)+0.9403
(b) temperature (° C.)=45.4833·(output voltage of the optical energy detector)+165.511.

29. The system of claim 15, further comprising an additional optical waveguide in optical communication with the optical splitter/combiner and the detector of optical energy.

30. The system of claim 15, wherein the computing device determines the density and/or temperature of the fluid based on an intensity of the reflection of the optical energy.

31. The system of claim 30, wherein the computing device determines the density and/or temperature of the fluid based on a predetermined relationship between the intensity of the reflection and the density and/or temperature of the fluid.

32. The system of claim 15, wherein the source of optical energy is communicatively coupled to the computing device.

33. The system of claim 15, wherein said tubular conduit has a first end fixed in position to a vessel containing the fluid and wherein the probes are fixed in position within said tubular conduit with a sealing plug provided at a free end region of said tubular conduit and wherein interfacing the optical fibers with the fluid includes fixing in position the interface of each optical fiber between the filter and said sealing plug relative to fluid flow in said tubular conduit.

34. The system of claim 33, wherein the mount further comprises a flange capable of being attached to a wall of a container that holds the fluid.

35. The system of claim 33, wherein the tubular conduit is curved by approximately ninety degrees.

36. The system of claim 33, wherein the mount further comprises a flange fixedly coupled to the tubular conduit, and the flange can be mounted on a bottom wall of a container that holds the fluid so that an end of the tube member is approximately perpendicular to a surface of the fluid.

* * * * *